United States Patent [19]

Giesecke et al.

[11] 4,111,918

[45] Sep. 5, 1978

[54] POLYPARABANIC ACID DERIVATIVES

[75] Inventors: Henning Giesecke, Cologne; Jürgen Hocker, Bergisch-Gladbach; Rudolf Merten, Leverkusen, all of Germany

[73] Assignee: Bayer Aktiengesellschaft, Germany

[21] Appl. No.: 804,608

[22] Filed: Jun. 8, 1977

[30] Foreign Application Priority Data

Jun. 9, 1976 [DE] Fed. Rep. of Germany ....... 2625721

[51] Int. Cl.² .............................................. C08G 18/00
[52] U.S. Cl. ...................................... 528/73; 548/307; 548/310

[58] Field of Search .................. 260/77.5 CH, 77.5 C, 260/77.5 R; 548/307, 310

[56] References Cited

U.S. PATENT DOCUMENTS

| | | | |
|---|---|---|---|
| 3,933,758 | 1/1976 | Patton | 260/77.5 CH |
| 4,005,056 | 1/1977 | Dunwald et al. | 260/77.5 CH |

*Primary Examiner*—M. J. Welsh
*Attorney, Agent, or Firm*—Connolly and Hutz

[57] ABSTRACT

New polyparabanic acid derivatives and their preparation by reacting $\Delta^2$-imidazolines with organic polyisocyanates.

7 Claims, No Drawings

POLYPARABANIC ACID DERIVATIVES

This invention relates to polyparabanic acid derivatives and to a process for the production thereof.

The polyparabanic acid derivatives according to the present invention contain the following repeating structural unit preferably from 2 to 100 times, in the molecule:

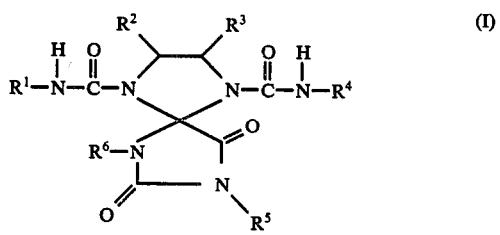

In general formula (I) above:
$R^1$, $R^4$, $R^5$ and $R^6$, which may be the same or different, each represents an optionally substituted aliphatic, aromatic or aliphatic-aromatic radical; and $R_2$ and $R_3$, which may be the same or different, each represents a hydrogen atom, or an optionally substituted aliphatic, aromatic or aliphatic-aromatic radical or together form a ring. The recurring units corresponding to general formula (I) are attached to one another through the radicals $R^1$ and/or $R^4$ and/or $R^5$ and/or $R^6$.

The monofunctional, difunctional or higher polyfunctional radicals $R^1$, $R^4$, $R^5$ and $R^6$ are preferably derived from optionally substituted aliphatic radicals containing from 2 to 20, preferably from 2 to 12 carbon atoms, such as alkyl radicals containing from 2 to 12 carbon atoms, optionally substituted aromatic radicals containing from 6 to 20, preferably from 6 to 16 carbon atoms, such as phenyl, naphthyl, diphenyl or diaryl ether radicals, radicals derived from alkyl or aryl ethers of organic or inorganic acids or optionally substituted aliphatic-aromatic radicals containing from 7 to 20 carbon atoms, such as xylene.

$R^2$ and $R^3$ preferably represent hydrogen or are derived from optionally substituted aliphatic radicals containing from 1 to 20 carbon atoms, preferably from 1 to 12 carbon atoms, wuch as alkyl radicals containing from 1 to 6 carbon atoms, cycloalkyl radicals containing from 5 to 7 carbon atoms, optionally substituted aromatic radicals containing from 6 to 20 carbon atoms, preferably from 6 to 16 carbon atoms, such as aryl radicals, for example phenyl, naphthyl, diphenyl, diphenyl ether radicals, or optionally substituted aliphatic-aromatic radicals, containing from 7 to 20 carbon atoms, such as benzyl. Radicals $R^2$ and $R^3$ may also be attached to one another to form a cycloaliphatic ring.

Substituents on the above-mentioned aliphatic, aliphatic-aromatic or aromatic radicals are, for example, aryl (preferably phenyl), CN, $NO_2$, alkyl mercapto and alkoxy groups preferably containing from 1 to 4 carbon atoms, carboxylic ester groups, preferably those with lower aliphatic alcohols, preferably containing from 1 to 8, especially up to 4 carbon atoms, and also the disubstituted amino group, preferably substituted by lower aliphatic radicals, preferably containing from 1 to 4 carbon atoms, halogens (preferably fluorine, chlorine, bromine), lower haloalkyl radicals (preferably containing from 1 to 4 carbon atoms, the halogen preferably being fluorine and/or chlorine) and, in the case of the aromatic radicals, also lower alkyl groups, preferably having from 1 to 4 carbon atoms.

The polyparabanic acid derivatives according to the present invention preferably have molecular weights of from 1000 to 50,000, more especially from 4000 to 30,000 (as measured by osmosis). They show characteristic IR-absorption bands at from 1720 to 1740 cm$^{-1}$ (strong) and at from 1780 to 1800 cm$^{-1}$ (weak), in addition to the urea carbonyl bands at from 1630 to 1700 cm$^{-1}$ (strong). A further object of the present invention is a process for the production of the inventive polyparabanic acids by reacting $\Delta^2$-imidazolines corresponding to the following general formula (II):

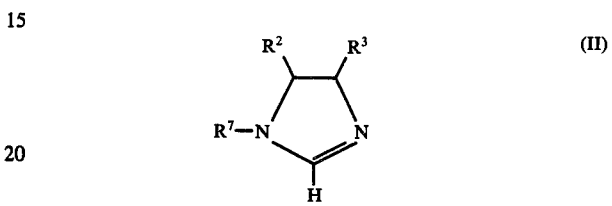

wherein
$R^2$ and $R^3$ are as defined above; and
$R^7$ represents a hydrogen atom or an optionally substituted aliphatic carbamoyl radical, preferably containing $C_2$-$C_{20}$, or aliphatic-aromatic carbamoyl radical, preferably containing $C_8$-$C_{20}$, or an aromatic carbamoyl radical; preferably containing $C_7$-$C_{21}$, with organic polyisocyanates.

In the context of the present invention, carbamoyl radicals are radicals corresponding to the following structure:

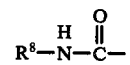

wherein
$R^8$ represents an optionally substituted aliphatic radical, preferably containing $C_1$-$C_{19}$ or aliphatic-aromatic radical, preferably containing $C_7$-$C_{19}$, or aromatic radical, preferably containing $C_6$-$C_{20}$.

The following $\Delta^2$-imidazolines are preferred for carrying out the process according to the present invention:
$\Delta^2$-imidazoline
4-methyl-$\Delta^2$-imidazoline
4-ethyl-$\Delta^2$-imidazoline
4-cyclohexyl-$\Delta^2$-imidazoline
4-phenyl-$\Delta^2$-imidazoline
4-(p-chlorophenyl)-$\Delta^2$-imidazoline
4,5-dimethyl-$\Delta^2$-imidazoline
5-ethyl-4-methyl-$\Delta^2$-imidazoline
5-methyl-4-phenyl-$\Delta^2$-imidazoline    hexahydrobenzimidazole
1-(methylcarbamoyl)-$\Delta^2$-imidazoline
1-(n-propylcarbamoyl)-$\Delta^2$-imidazoline
1-(cyclohexylcarbamoyl)-$\Delta^2$-imidazoline
1-(phenylcarbamoyl)-$\Delta^2$-imidazoline
1-(3,4-dichlorophenylcarbamoyl)-$\Delta^2$-imidazoline
1-(p-nitrophenylcarbamoyl)-$\Delta^2$-imidazoline
1-(methylcarbamoyl)-4-methyl-$\Delta^2$-imidazoline
1-(phenylcarbamoyl)-hexahydrobenzimidazole
1-(p-tolylcarbamoyl)-5-(naphthyl-1)-$\Delta^2$-imidazoline Organic polyisocyanates containing at least 2 NCO-groups of the present invention are: aliphatic $C_2$-$C_{20}$ polyisocyanates, cycloaliphatic $C_5$–$C_{12}$ polyisocyanates, araliphatic $C_7$–$C_{20}$ polyisocyanates, aromatic $C_6$–$C_{20}$ polyisocyanates and heterocyclic $C_4$–$C_{20}$ polyisocyanates of the type described, for example, by W. Siefgen in Justus Liebigs Annalen der Chemie, 562, pages 75 to 136, for example ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and 1,4-diisocyanate and mixtures of these isomers, 1-isocyanato-3,3,5-trimethyl-5-isocyanatomethyl cyclohexane (DAS No. 1,202,785), 2,4- and 2,6-hexahydrotolylene diisocyanate and mixtures of these isomers, hexahydro-1,3- and/or 1,4-phenylene diisocyanate, perhydro-2,4'- and/or -4,4'-diphenyl methane diisocyanate, 1,3- and 1,4-phenylene diisocyanate, 2,4- and 2,6-tolylene diisocyanate and mixtures of these isomers, diphenyl methane-2,4'- and/or, -4,4'-diisocyanate, naphthylene-1,5-diisocyanate, triphenyl methane-4,4',4''-triisocyanate, polyphenyl-polymethylene polyisocyanates of the type which may be obtained by condensing aniline and formaldehyde, followed by phosgenation, and described, for example, in British Pat. Nos. 874,430 and 848,671, perchlorinated aryl polyisocyanates of the type described, for example, in German Auslegeschrift No. 1,157,601, polyisocyanates containing carbodiimide groups of the type described in German Pat. No. 1,092,007, diisocyanates of the type described in U.S. Pat. No. 3,492,330, polyisocyanates containing allophanate groups of the type described, for example, in British Pat. No. 994,890, Belgian Pat. No. 761,626 and Published Dutch Patent Application No. 7,102,524, polyisocyanates containing isocyanurate groups of the type described, for example, in German Pat. Nos. 1,022,789; 1,222,067 and 1,027,394 and in German Offenlegungsschrift Nos. 1,929,034 and 2,004,048, polyisocyanates containing urethane groups of the type described, for example, in Belgian Pat. No. 752,261 or in U.S. Pat. No. 3,394,164, polyisocyanates containing acylated urea groups according to German Pat. No. 1,230,778, polyisocyanates containing biuret groups of the type described, for example, in German Pat. No. 1,101,394, in British Pat. No. 889,050 and in French Pat. No. 7,017,514, polyisocyanates produced by telomerisation reactions of the type described, for example, in Belgian Pat. No. 723,640, polyisocyanates containing ester groups of the type described, for example, in British Pat. Nos. 956,474 and 1,072,956, in U.S. Pat. No. 3,567,763 and in German Pat. No. 1,231,688, reaction products of the above-mentioned isocyanates with acetals according to German Pat. No. 1,072,385.

It is also possible to use the distillation residues containing isocyanate groups which are obtained in the manufacture of isocyanates on an industrial scale, optionally in solution in one or more of the above-mentioned polyisocyanates. Mixtures of the above-mentioned polyisocyanates may also be used.

In general, it is particularly preferred to use the polyisocyanates readily obtainable on a commercial scale, for example 2,4- and 2,6-tolylene diisocyanate, and mixtures of these isomers, ("TDI"), polyphenyl-polymethylene polyisocyanates of the type obtained by condensing aniline and formaldehyde, followed by phosgenation ("crude MDI") and polyisocyanates containing carbodiimide groups, urethane groups, allophanate groups, isocyanurate groups, urea groups or biuret groups ("modified polyisocyanates").

In order to reduce the degree of crosslinking of the polyparabanic acid derivatives, it is also possible, in addition to polyisocyanates, to use the corresponding aliphatic or aromatic monoisocyanates.

The present process is preferably carried out by reacting the starting components in an organic solvent at a temperature of from $-20°$ to $+400°$ C., the polymer formed remaining in solution or precipitating. It may be isolated by distilling off the solvent. The starting substances may be used in such quantities that from 0.5 to 10 moles, preferably about 4 moles, of isocyanate groups are available per mole of $\Delta^2$-imidazoline. Solvents suitable for use in the process are compounds which are inert to NCO-groups, for example aromatic hydrocarbons, chlorinated aromatic hydrocarbons, benzonitrile, aliphatic hydrocarbons, esters and ketones. Particularly suitable solvents are toluene, xylene, mesitylene, chlorobenzene, dichlorobenzene, N-methyl pyrrolidone, dimethyl formamide, dimethyl acetamide, hexamethyl phosphoric acid triamide, tetramethyl urea, nitromethane and nitrobenzene. However, the components may also be reacted in the absence of solvents.

The reaction times are generally from 15 minutes to 100 hours, preferably from 1 to 20 hours, although in certain cases they may even be longer or shorter.

The reaction is carried out at temperatures of from $-20°$ to $+400°$ C., depending upon the starting material. The reaction is preferably carried out at temperatures of from $60°$ to $350°$ C. and, with particular preference, at temperatures of from $80°$ to $250°$ C.

Polymerisation may be carried out in the presence of the acidic or basic catalyts normally used, for example metal alcoholates and tertiary amines.

The thus-obtained polyparabanic acid derivatives may contain terminal NCO groups and, hence, provide for crosslinking with the compounds normally used in isocyanate chemistry, such as polyols or polyamines, or for crosslinking to form isocyanurate structures. Chain-lengthening with formation of carbodiimide or uretdione structures is also possible.

Other polymeric compounds, for example polyesters, polyethers, polyamides, polyurethanes, polyolefins, polyacetals, polyepoxides, polyimides, polyamidines, polyimide diisocyanates, polyhydrantoins, may also be used in known manner in the process according to the present invention. These polymers may be added to the finished polymers according to the present invention, or they may also be copolymerised with them.

In one particular embodiment of the process according to the present invention, polyesters containing hydroxyl groups or polyethers are used in conjunction with excess quantities of isocyanate components, this results in combined parabanic acid and urethane formation. For this purpose, mixtures of, for example, polyhydroxyl compounds, polyisocyanate (derivative) and a compound according to general formula (II) are converted into the plastics material in a simultaneous final operation, optionally after the precondensation of two of these components.

The polyesters containing hydroxyl groups used in accordance with the present invention are the known types which may be obtained in the conventional way from carboxylic acids, for example succinic acid, adipic acid, sebacic acid, phthalic acid, isophthalic acid, terephthalic acid and oleic acid, by reaction with polyhydric alcohols, for example glycol, diethylene glycol, triethylene glycol, propylene glycol, dipropylene glycol, glycerol, trimethylol propane and pentaerythritol.

The polyarabanic acid derivatives according to the present invention and mixtures thereof with other polymers are temperature-resistant plastics having excellent mechanical properties which may be used as lacquers, and films. They may contain the additives normally used for plastics, such as fillers, pigments, anti-oxidants and plasticizers.

EXAMPLE 1

7 Parts by weight, of $\Delta^2$-imidazoline in 7 parts, by weight, of N-methyl pyrrolidone are added dropwise over a period of 30 minutes at 125° C. to 50 parts by weight, of hexamethylene diisocyanate in 550 parts by weight, of chlorobenzene, followed by stirring for 1 hour at 135° C. Subsequent filtration leaves 21 parts, by weight, of a solid polymer which exhibits the IR-absorption bands characteristic of parabanic acid derivatives at 1774 cm$^{-1}$ (weak) and 1712 cm$^{-1}$ (strong), in addition to the urea carbonyl band at 1662 cm$^{-1}$ (strong). Viscosity of a 14% solution in m-cresol at 25° C.: 50 cP.

EXAMPLE 2

35 Parts by weight, of $\Delta^2$-imidazoline, dissolved in 35 parts by weight, of N-methyl pyrrolidone, are added dropwise over a period of 15 minutes at 140° C to 840 parts by weight, of hexamethylene diisocyanate, followed by stirring for 3 hours at 140° C. Concentration of the solution in a high vacuum at 110° C. leaves 392 parts by weight, of a prepolymer containing 22.0% of NCO. Viscosity of a 75% solution in ethylene glycol monomethyl ether acetate at 25° C.: 570 cP.

50 Parts by weight, of this 75% solution of the prepolymer are mixed with 40 parts by weight, of a 65% solution of a polyester containing 5.2% of hydroxyl groups, produced from 52 parts by weight, of phthalic acid anhydride, 0.6 part, by weight, of maleic acid anhydride and 54 parts by weight, of trimethylol propane, in ethyl glycol acetate and 0.1 part, by weight, of Sn(II) dioctoate. A quick-drying lacquer is obtained.

EXAMPLE 3

7 Parts, by weight, of $\Delta^2$-imidazoline, dissolved in 7 parts, by weight, of N-methyl pyrrolidone, are added dropwise over a period of 30 minutes at 120° C. to a mixture of 67 parts, by weight, or hexamethylene diisocyanate and 50 parts, by weight, of cyclohexyl isocyanate, followed by stirring for 1 hour at 120° C. Concentration of the solution in a high vacuum at 100° C. leaves 60 parts, by weight, of a viscous yellow prepolymer containing NCO-groups. Viscosity at 40° C.: 23000 cP.

EXAMPLE 4

12.4 Parts, by weight, of hexahydrobenzimidazole, dissolved in 6 parts, by weight, of N-methyl pyrrolidone, are added dropwise over a period of 30 minutes at 100° C. to 33.6 parts, by weight, of hexamethylene diisocyanate in 200 parts, by weight, of N-methyl pyrrolidone, followed by stirring for 1 hour at 100° C. Concentration of the solution in a high vacuum leaves 40 parts, by weight, of a solid polymer which exhibits the IR-Absorption bands characteristic of parabanic acid derivatives at 1775 cm$^{-1}$ (weak) and 1721 cm$^{-1}$ (strong).

EXAMPLE 5

7 Parts, by weight, of $\Delta^2$-imidazoline, diisolved in 7 parts, by weight, of N-methyl pyrrolidone, are added dropwise over a period of 15 minutes at 135° C. to 26 parts of an isomer mixture of 80 parts of 2,4-tolylene diisocyanate and 20 parts of 2,6-tolylene diisocyanate in 260 parts, by weight, of xylene, followed by stirring for 30 minutes at 135° C. Subsequent filtration leaves 28 parts, by weight, of a solid polymer which exhibits the IR-absorption bands characteristic of parabanic acid derivatives at 1790 cm$^{-1}$ (weak) and 1728 cm$^{-1}$ (strong). Viscosity of a 14% solution in cresol at 25° C.: 70 cP.

EXAMPLE 6

7 Parts, by weight, of $\Delta^2$-imidazoline, dissolved in 7 parts, by weight, of N-methyl pyrrolidone, are added dropwise over a period of 15 minutes at 165° C. to 35 parts of an isomer mixture of 80 parts of 2,4-tolylene diisocyanate and 20 parts of 2,6-tolylene diisocyanate in 360 parts, by weight, of o-dichlorobenzene, followed by stirring for 1 hour at 165° C. 40 parts, by weight, of a solid polymer which exhibits the IR-absorption bands characteristic of parabanic acid derivatives at 1792 cm$^{-1}$ (weak) and 1735 cm$^{-1}$ (strong) are obtained. Viscosity of a 14% solution in cresol at 25° C.: 70 cP.

EXAMPLE 7

7 Parts, by weight, of $\Delta^2$-imidazoline, dissolved in 7 parts, by weight, of N-methyl pyrrolidone, are added dropwise over a period of 30 minutes at 125° C. to 35 parts, by weight, of 2,4-tolylene diisocyanate in 350 parts, by weight, of chlorobenzene following the addition of 0.2 part, by weight, of diazabicyclo-(2,2,2)-octane. The mixture is then stirred for 30 minutes at 125° C. Subsequent filtration leaves 35 parts, by weight, of a solid polymer. Viscosity of a 14% solution in cresol at 25° C.: 65 cP.

EXAMPLE 8

7 Parts, by weight, of $\Delta^2$-imidazoline are added in portions over a period of 30 minutes at 165° C. to 50 parts, by weight, of diphenyl methane-4,4'-diisocyanate, followed by stirring for 1 hour at 165° C. Filtration leaves 44 parts, by weight, of a solid polymer which exhibits the IR-absorption bands characteristic of parabanic acid derivatives at 1794 cm$^{-1}$ (weak) and 1729 cm$^{-1}$ (strong), in addition to a urea carbonyl band at 1688 cm$^{-1}$ (strong).

EXAMPLE 9

8.4 Parts, by weight, of 4-methyl-$\Delta^2$-imidazoline are added dropwise over a period of 30 minutes at 125° C. to 35 parts, by weight, of 2,4-tolylene diisocyanate in 350 parts, by weight, of chlorobenzene, followed by stirring for 1 hour at 125° C. Filtration leaves 37 parts, by weight, of a solid polymer which exhibits the IR-absorption bands characteristic of parabanic acid derivatives at 1791 cm$^{-1}$ (weak) and 1728 cm$^{-1}$ (strong). Viscosity of a 14% solution in cresol at 25° C.: 60 cP.

EXAMPLE 10

7 Parts, by weight, of $\Delta^2$-imidazoline dissolved in 7 parts, by weight, of N-methyl pyrrolidone are added dropwise over a period of 10 minutes at 100° C. to 222 parts, by weight, of isophorone diisocyanate, followed by stirring for 2 hours at 100° C. Concentration of the pale yellow solution in a high vacuum at 170° C. gives 79 parts, by weight, of a brittle resin containing 13.9% of NCO groups which exhibits the IR-absorption bands characteristic of parabanic acid derivatives at 1778 cm$^{-1}$ (weak) and 1722 cm$^{-1}$ (strong).

EXAMPLE 11

4 Parts, by weight, of 1-cyclohexylcarbamoyl-$\Delta^2$-imidazoline are dissolved in 5 parts, by weight, of hexamethylene diisocyanate and 1 part, by weight, of N-methyl pyrrolidone. The solution is coated onto an Erichsen plate (180 × 70 × 0.2 mm) and stoved for 10 minutes at 220° C. A firmly adhering lacquer having a softening temperature of from 220° to 260° C. is obtained.

What we claim is:

1. Polyparabanic acid derivatives which contain the following repeating structural unit from 2 to 100 times:

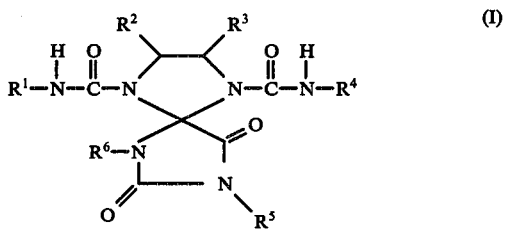

wherein
$R^1$, $R^4$, $R^5$ and $R^6$, which may be the same or different, each represents an optionally substituted aliphatic, aromatic or aliphatic-aromatic mono- or poly-functional radical; and
$R^2$ and $R^3$, which may be the same or different, each represents a hydrogen atom or an optionally substituted aliphatic, aromatic or aliphatic-aromatic radical, or may together form a ring.

2. Polyparabanic acid derivatives as claimed in claim 1 which have a molecular weight of from 1,000 to 50,000.

3. Polyparabanic acid derivatives as claimed in claim 1, wherein $R^1$, $R^4$, $R^5$ is an optionally substituted aliphatic radical containing from 2 to 20 carbon atoms, an optionally substituted aromatic radical containing 6 to 20 carbon atoms or an optionally substituted aliphatic aromatic radical containing 7 to 20 carbon atoms and $R^2$ and $R^3$ is hydrogen or an optionally substituted aliphatic radical containing from 1 to 20 carbon atoms, an optionally substituted aromatic radical containing from 6 to 20 carbon atoms or an optionally substituted aliphatic-aromatic radical with 7 to 20 carbom atoms.

4. A process for the preparation of polyparabanic acid derivatives as claimed in claim 1 wherein a $\Delta^2$-imidazoline corresponding to the formula:

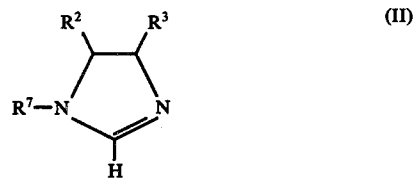

wherein $R^2$ and $R^3$ are as defined in claim 1; and $R^7$ represents a hydrogen atom or a carbamoyl radical of the formula

wherein $R^8$ is an optionally substituted aliphatic, aliphatic-aromatic or aromatic radical is reacted with an organic polyisocyanate at a temperature of from $-20°$ to $-400°$ C.

5. A process as claimed in claim 4 wherein the reaction is carried out at a temperature of from 60° to 350° C.

6. A process as claimed in claim 5 wherein the reaction is carried out at a temperature of from 80° to 250° C.

7. A process as claimed in claim 4 wherein the reaction is carried out using from 0.5 to 10 moles of isocyanate per mole of $\Delta^2$-imidazoline.

* * * * *